US011602278B2

(12) United States Patent
Johanning

(10) Patent No.: US 11,602,278 B2
(45) Date of Patent: Mar. 14, 2023

(54) APPARATUS FOR ASSESSING USER FRAILTY

(71) Applicant: The Board of Regents of the University of Nebraska, Lincoln, NE (US)

(72) Inventor: Jason M. Johanning, Omaha, NE (US)

(73) Assignee: Board of Regents of the University of Nebraska, Lincoln, NE (US)

(\*) Notice: Subject to any disclaimer, the term of this patent is extended or adjusted under 35 U.S.C. 154(b) by 334 days.

(21) Appl. No.: 16/230,369

(22) Filed: Dec. 21, 2018

(65) Prior Publication Data

US 2019/0192013 A1 Jun. 27, 2019

Related U.S. Application Data

(60) Provisional application No. 62/610,669, filed on Dec. 27, 2017.

(51) Int. Cl.
*A61B 5/0205* (2006.01)
*G06F 9/451* (2018.01)
(Continued)

(52) U.S. Cl.
CPC ............ *A61B 5/02055* (2013.01); *A61B 5/01* (2013.01); *A61B 5/1118* (2013.01);
(Continued)

(58) Field of Classification Search
CPC ....... A61B 5/01; A61B 5/02055; A61B 5/024; A61B 5/1118; A61B 5/14551;
(Continued)

(56) References Cited

U.S. PATENT DOCUMENTS 5,570,301 A 10/1996 Barrus
8,211,014 B2 7/2012 David et al.
(Continued)

FOREIGN PATENT DOCUMENTS

WO 2017015179 A1 1/2017
WO 2017039929 A1 3/2017

OTHER PUBLICATIONS

Cooper, Zara, MD, MSc et al., "Comparison of Frailty Measures as Predictors of Outcomes After Orthopedic Surgery", The American Geriatrics Society, JAGS 64:2464-2471, 2016.
(Continued)

*Primary Examiner* — Carl H Layno
*Assistant Examiner* — Jane C Kalinock
(74) *Attorney, Agent, or Firm* — Nasr Patent Law LLC; Faisal K. Abou-Nasr

(57) ABSTRACT

An apparatus for assessing user frailty is disclosed. In embodiments, the apparatus includes a housing that defines (or is defined by) a body and a handle coupled to the body. The apparatus includes a force sensor at least partially disposed within the handle. The apparatus further includes an inertial sensor at least partially disposed within the housing. The apparatus may further include a user interface device disposed within a cavity of the body. The user interface device may be coupled to the force sensor and the inertial sensor via one or more signal paths. In embodiments, the user interface device includes a controller with a touch-screen coupled to the controller.

20 Claims, 13 Drawing Sheets

(51) Int. Cl.

| | |
|---|---|
| *G16H 40/63* | (2018.01) |
| *A61B 5/00* | (2006.01) |
| *A61B 5/22* | (2006.01) |
| *A61B 5/11* | (2006.01) |
| *A61B 5/01* | (2006.01) |
| *A61B 5/1455* | (2006.01) |
| *A61B 5/021* | (2006.01) |
| *A61B 5/024* | (2006.01) |

(52) U.S. Cl.
CPC .......... *A61B 5/14551* (2013.01); *A61B 5/225* (2013.01); *A61B 5/748* (2013.01); *G06F 9/451* (2018.02); *G16H 40/63* (2018.01); *A61B 5/021* (2013.01); *A61B 5/024* (2013.01); *A61B 2560/0456* (2013.01); *A61B 2562/0219* (2013.01)

(58) Field of Classification Search
CPC . A61B 5/225; A61B 5/748; A61B 2560/0456; A61B 2562/0219; A61B 2560/0431; A61B 5/1072; G06F 9/451; G16H 15/00; G16H 40/63; G16H 50/30
USPC ...................................... 600/300–301; 606/1
See application file for complete search history.

(56) References Cited

U.S. PATENT DOCUMENTS

| | | | | |
|---|---|---|---|---|
| 8,475,367 | B1* | 7/2013 | Yuen | A61B 5/02007 |
| | | | | 600/300 |
| 9,030,828 | B2 | 5/2015 | Lindblad et al. | |
| 2002/0044059 | A1 | 4/2002 | Reeder et al. | |
| 2004/0186358 | A1 | 9/2004 | Chernow et al. | |
| 2007/0136102 | A1 | 6/2007 | Rodgers | |
| 2010/0168526 | A1* | 7/2010 | Nishimura | A61B 5/14532 |
| | | | | 600/300 |
| 2013/0001435 | A1* | 1/2013 | Engelhardt | A61L 2/20 |
| | | | | 250/455.11 |
| 2013/0110475 | A1* | 5/2013 | Greene | G16H 50/30 |
| | | | | 703/2 |
| 2015/0332004 | A1 | 11/2015 | Najafi et al. | |
| 2016/0042123 | A1* | 2/2016 | Meyer | A61B 5/4082 |
| | | | | 434/362 |
| 2017/0351825 | A1* | 12/2017 | Geleijnse | G16H 40/63 |
| 2020/0034501 | A1* | 1/2020 | Duff | G01S 5/02 |

OTHER PUBLICATIONS

Fritz, Stacy L., MSPT, PhD et al., "Measuring Walking Speed Clinical Feasibility and Reliability", Topics in Geriatric Rehabilitation, vol. 28, No. 2, 91-96, Apr.-Jun. 2012.

Leong, Darryl P. et al., "Prognostic value of grip strength: findings from the Prospective Urban Rural Epidemiology (PURE) study", Lancet 2015, vol. 386, 266-273, Jul. 18, 2015.

Lusardi, Michelle M., PT, DPT, PhD, "Is Walking Speed a Vital Sign? Absolutely", Topics in Geriatric Rehabilitation, vol. 28, No. 2, 67-76, Apr.-Jun. 2012.

Sayer, Avan Aihie et al., "Grip strength and mortality: a biomarker of aging?", Lancet, vol. 386, 226-227, Jul. 18, 2015.

Schiller, Ben, "You Can Tell How Long Someone is Going to Live by the Strength of Their Grip", https://www.fastcoexist.com/3046503/you-can-tell-how-long-someone-is-going-to-live-by-the-strength-of-their-grip, 1-4, May 27, 2015.

Sprint, Gina et al., "Towards Automating Clinical Assessments: A Survey of the Timed Up and Go (TUG)", School of Electrical Engineering and Computer Science, Washington State University, Pullman, WA, St. Luke's Rehabilitation Institute, Spokane, WA, 1-42.

International Search Report and Written Opinion dated Apr. 1, 2019 for PCT/US2018/067297.

* cited by examiner

APPARATUS FOR ASSESSING USER FRAILTY

CROSS-REFERENCE TO RELATED APPLICATIONS

The present application claims the benefit under 35 U.S.C. § 119(e) of U.S. Provisional Application Ser. No. 62/610,669, filed Dec. 27, 2017, and titled "Rapid Patient Frailty Assessment System," which is incorporated by reference herein in its entirety.

BACKGROUND

Frailty of a patient is a critical metric when providing safe care of the patient at all levels of the healthcare system. For example, the frailty of a patient may determine whether a patient is fit to undergo surgical operations, capable of performing rehabilitation exercises, or the like. For instance, patient frailty may be used as a predictor for a 180-day mortality probability of a patient undergoing a particular surgical operation. Increasing the rapidity at which patient information is obtained and assessed, and the ease with which the patient information may be accessed, may result in an increased chance for the patient to survive select medical procedures or avoidance of medical procedures that pose risk with little to no benefit to the patient.

SUMMARY

An apparatus for assessing user frailty is disclosed. In embodiments, the apparatus includes a housing that defines (or is defined by) a body and a handle coupled to the body. The apparatus includes a force sensor at least partially disposed within the handle. The apparatus further includes an inertial sensor at least partially disposed within the housing. The apparatus may further include a user interface device disposed within a cavity of the body. The user interface device may be coupled to the force sensor and the inertial sensor via one or more signal paths. In embodiments, the user interface device includes a controller with a touchscreen coupled to the controller.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Figure 1:
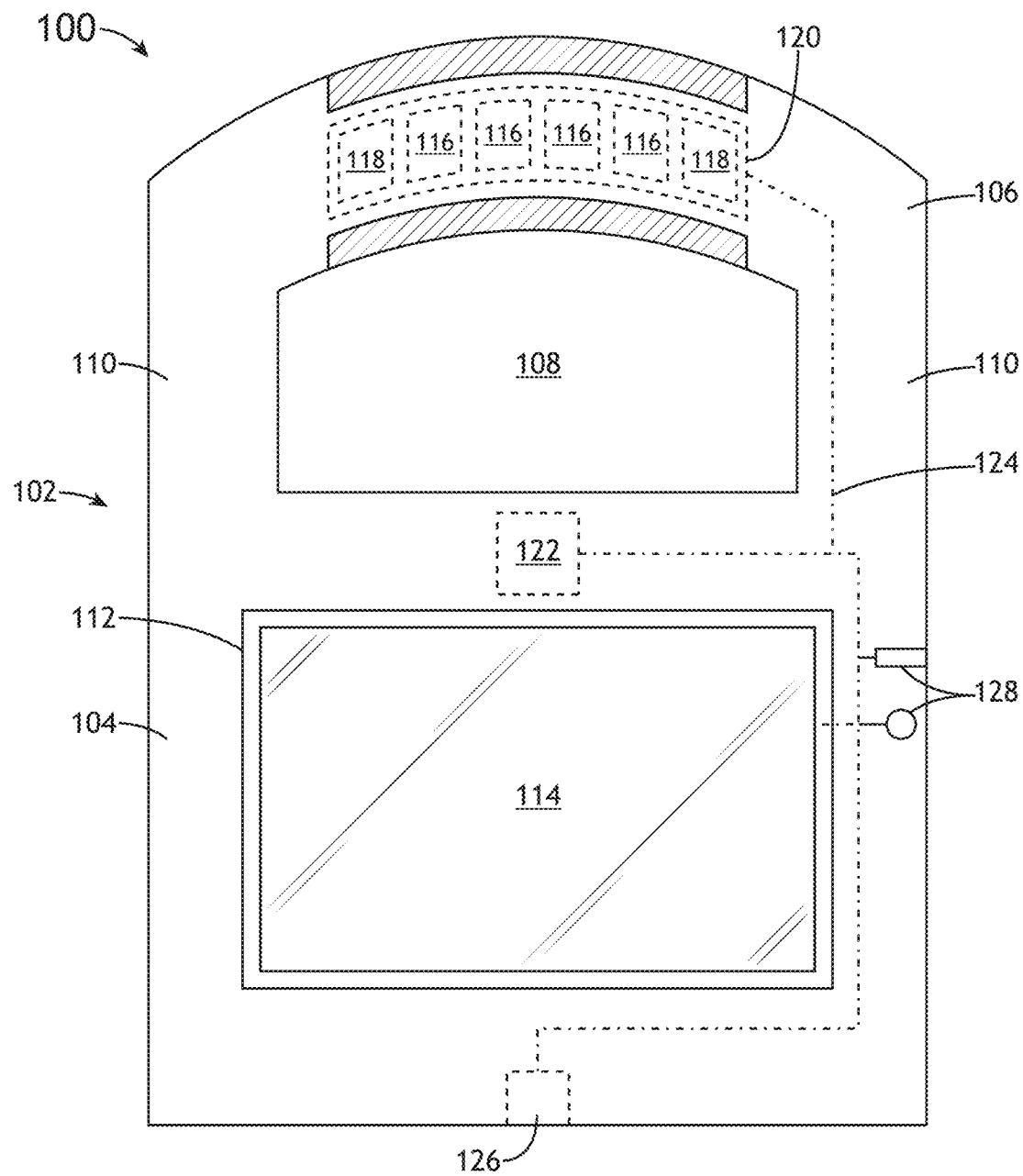
FIG. 1 is a frontal view of an apparatus for assessing user frailty, in accordance with an example embodiment of the present disclosure.

Several assessment tools exist to assess muscle strength and mobility in the medical field. These assessment tools can be used for both diagnostic and prognostic purposes. These assessments can also be utilized in assessing frailty. Some of the most widely used assessments include grip strength, walking speed, and timed-up-and-go.

A grip strength test measures the maximum isometric strength of the hand and forearm muscles. Grip strength is a known predictor of all-cause mortality, cardiovascular mortality, incident cardiovascular disease, myocardial infarction, and stroke. Grip strength can be used to diagnose diseases, to evaluate and compare treatments, to document progression of muscle strength, and to provide pre and postoperative feedback or feedback during the rehabilitation process as a measure indicating the level of hand function. Handgrip strength can be measured by the amount of static force in pounds that the hand can squeeze around a handgrip dynamometer. These results can be compared to known normative average values for both men and women.

The walking speed test is a known performance measure used to assess walking speed over a short distance. Walking speed is an indicator that can be used to determine functional mobility, gait and vestibular function; can be predictive of future events such as mortality and functional decline; is a predictor of outcomes of rehabilitation; and can reflect underlying neuromotor physiological processes. Walking speed can also be an indicator of overall comorbid burden of illness. Walking speed is measured in meters per second (m/s) as the subject (patient) walks around a walking path. The subject's speed is measured over the middle portion of the path, allowing a portion of the path to account for acceleration and deceleration. The ideal length of the walking path is 20 meters, with walking speed recorded over the middle 10 meters. Many clinical and research settings employ walking speed tests of different lengths, but recent research exists examining the accuracy of shorter distances and strongly supports a 4 meter walk as adequate. Measured walking speed can be compared against normative age and gender data. Those walking at speeds less than 6 m/s are most vulnerable to adverse health events and early mortality. Walking speed can currently be measured by a stopwatch with visual estimation of starting and stopping points, automatic timers, or pressure-activated walkways (e.g., GAITRite systems, CIR systems, etc.). Walking speed has strong clinometric characteristics and many researchers consider it to be a vital sign.

Measurements of other temporal and spatial elements of gait (e.g., stride and step length, stride symmetry, single and double-limb support, and step width) can be indicative of falls and frailty in the elderly. These measurements can provide a more in-depth analysis of health status than measuring walking speed alone. Gait characteristics can be measured by standardized visual assessment tools (e.g., Tinetti Test, Dynamic Gait Index, Functional Gait Assessment, etc.), electromyography, floor-to-floor reaction forces, 2-dimensional versus 3-dimensional motion analysis, or body-worn kinematic sensors. The validity of these measurement tools differs depending on age and disease state of the subject (patient).

The timed-up-and-go (TUG) test is a known assessment of basic mobility skills. The TUG test is a measurement of the time in seconds for a person to rise from sitting in a standard arm chair, walk 3 meters at a normal pace, turn, walk back to the chair, and sit down. This duration is indicative of a subject's ambulatory abilities, balance, and possibly risk of falling. The test has been used in many patient populations, including the elderly, arthritis patients, stroke patients, vertigo patients, and Parkinson's disease patients. There are many methods of administering the TUG test including a timed visual test, video-conferencing, Kinect sensors, wearable sensors (e.g., inertial measurement units, iTUG, surface electromyography, accelerators, magnetometers, etc.), mobile device sensors (e.g., smartphone sensors, etc.), and ambient sensors (e.g., aTUG, etc.). Testing methods incorporating technology provide a more thorough assessment, as these devices are capable of capturing elements in addition to TUG duration (e.g., maximum angular velocity during sit-to-stand and stand-to-sit, component duration, maximum trunk angle change, joint angles, average step time, maximum step time, number of steps, cadence, etc.), and help compensate for movement strategies employed by subjects. Wearable sensors and mobile device sensors also allow for in-home assessment by the subjects themselves. While TUG is an important and beneficial standardized test, its limitations include low test-retest reliability due to differences in the chair used, differences in the subject's footwear, the use of assistive devices (e.g., walker, cane, etc.), and medication changes.

Additionally, a combination of the above assessments can be used to perform multifaceted assessment. Such an assessment can be used to assess for multidimensional disease states, such as frailty. Frailty is a multidimensional geriatric syndrome characterized by increased vulnerability to stressors as a result of reduced capacity of different physiological systems. It has been associated with an increased risk of adverse health-related outcomes in older persons, including falls, disability, hospitalizations morbidity, mortality, and has further been associated with biological abnormalities (e.g., biomarkers of inflammation). The occurrence of frailty increases incrementally with advancing age, is more common in older women than men, and is more common among those of lower socio-economic status. Frail older adults are at high risk for major adverse health outcomes, including disability, falls, institutionalization, hospitalization, and mortality. Frailty can also be indicative of underlying pathogenesis. Frailty is highly predictive of poor surgical outcomes including death, disability and institutionalization. Associations between specific disease states are associated with frailty, including cardiovascular disease, diabetes mellitus, renal insufficiency and other diseases in which inflammation is prominent.

Frailty can be assessed in a variety of ways. The most commonly used assessment used primarily in the research setting is the frailty phenotype (Fried assessment), which is defined by the presence of three of five symptoms including poor muscle strength, slow gait speed, unintentional weight loss, exhaustion, and sedentary behavior. Validated frailty assessment tools include the Cardiovascular Health Study frailty screening measure, the FRAIL questionnaire screening tool, the Clinical Frailty Scale, and the Gérontopôle Frailty Screening Tool. Monitoring the subject's vital signs (e.g., temperature, heart rate, blood pressure, etc.) may also be necessary. A comprehensive geriatric assessment may be necessary to adequately assess frailty. An accurate assessment of frailty allows for the implementation of interventions (e.g., nutrition changes, exercise plans) that can lead to reduced hospital stays and health care costs.

Despite the known efficacy of a variety of assessment tools for muscle strength, mobility, and frailty, the utilization of these assessment tools in practice is limited by feasibility. Performing a comprehensive body of assessments currently requires time, physical space, and multiple pieces of medical equipment. A lack of knowledge in interpreting assessment tools may also be a barrier to utilization of assessments. Walking speed tests, in particular, can require a significant amount of space (e.g., 20 meter walkway ideally) to administer, and automatic timers or pressure-activated electronic walkways necessary to enhance accuracy can be costly. Further, developing a complete assessment of a subject's health status with currently available assessment tools often requires repeated testing of the subject, or multiple practitioners administering the test. For example, it would be difficult for one practitioner to both visually assess walking speed and other characteristics of gait simultaneously. Additionally, automated assessments provide enhanced accuracy because they permit continuous and calibrated measurements. However, there is a lack of automated assessment tools that can measure multiple variables simultaneously.

Various embodiments of this disclosure are directed to an apparatus for assessing user frailty. More particularly, embodiments disclosed herein are directed to an apparatus for assessing user frailty and corresponding systems and methods incorporating the apparatus, where the apparatus is able to collect and report data related to a frailty of a user.

FIG. 1 illustrates an example embodiment of an apparatus 100 for assessing user frailty. The apparatus 100 includes a housing 102. The housing 102 may include a body 104 with a handle 106 coupled to the body 104. The apparatus 100 may include a cavity 108 defined by the body 104 and the handle 106. For example, a user may interact with the apparatus 100 by inserting a hand and grabbing onto the handle 106 during an assessment of the user's frailty.

The handle 106 may be coupled to the body 104 by one or more legs 110. For example, the apparatus 100 may include two legs 110 that couple the handle 106 to the body 104. In some embodiments, the handle 106 may be detached from the body 104 via a point of detachment along the one or more legs 110. It is noted herein the cavity 108 may be defined by the body 104, the handle 106, and the one or more legs 110.

The apparatus 100 may include one or more cushion pads. The one or more cushion pads may be coupled to the handle 106, and may operate as a cushion or grip for a user without interfering with any operational capabilities of the apparatus 100 (e.g., data collection, or the like). For example, the one or more cushion pads may be coupled to one or more surfaces of the handle 106. By way of another example, the one or more cushion pads may be integrated (e.g., at least partially embedded) into the one or more surfaces of the handle 106. The one or more cushion pads may be coupled to the body 104, and may operate as a cushion against impact damage for the apparatus 100.

The housing 102 may be fabricated and/or coated with an anti-microbial material. For example, the housing 102 may be fabricated from a plastic embedded within metal ions (e.g., copper ions ($Cu^{2+}$), silver ions ($Ag^{2+}$), or the like).

The apparatus 100 includes a cavity 112 defined within the body 104. A user interface device 114 can be disposed within the cavity 112. The user interface device 114 may include a personal electronic device or mobile device. For example, the personal electronic device may include a handheld computer such as, but not limited to, a smartphone, a tablet, a phablet, or the like.

The user interface device 114 may be integrated (e.g., at least partially embedded) within the cavity 112. For example, the user interface device 114 may be fully embedded within the cavity 112. For instance, a surface of the user interface device 114 may be flush with a surface of the body 104. In addition, the surface of the user interface device 114 may be set a select distance below the surface of the body 104.

The cavity 112 may be sealed from moisture, dust, or other debris by a cover layer (e.g., a transparent cover layer) and/or a gasket material (e.g., rubber, foam, resin, and/or epoxy) disposed about the user interface device 114 to seal the space between the user interface device 114 and the cavity 112. The cover layer may make up a portion (e.g., an outermost layer) of the user interface device 114. The cover layer may extend over the user interface device 114 and at least a portion of a surface of the housing 102 (e.g., the body 104). The cover layer may extend over the cavity 112 and the entire surface of the housing 102 (e.g., the body 104) so that the user interface device 114 is seamlessly integrated within the surface of the housing 102 (e.g., the body 104) and is protected from spills or any other form of moisture or debris that can potentially damage the user interface device 114. The cover layer may allow and/or transmit tactile input into the user interface 114.

The apparatus 100 includes one or more sensors. For example, the apparatus 100 includes one or more force sensors 116, where the one or more force sensors 116 may be utilized to measure one or more parameters or metrics indicative of a user's frailty. For example, the one or more parameters or metrics may include, but are not limited to, grip strength. For instance, the one or more force sensors 116 may include and/or may be configured as a dynamometer. In embodiments, the force sensors 116 may include, but are not limited to, one or more force sensor pads, force transducers, force sensing resistors, piezoelectric force sensors, or any combination thereof.

The apparatus 100 may further include one or more additional sensors 118. For example, the apparatus 100 may include an inertial sensor (e.g., accelerometer, gyroscope, or the like), where the inertial sensor may be utilized to measure one or more parameters or metrics indicative of to a user's frailty. In some embodiments, the one or more additional sensors 118 may additionally or alternatively include, but are not limited to, a blood oxygen sensor (e.g., a pulse oximeter), a blood pressure sensor, a heartrate sensor, a temperature sensor (e.g., a thermometer), or any combination thereof. The one or more additional sensors 118 can also include, but are not limited to, a motion sensor (e.g., a camera, or the like), an infrared (IR) sensor (e.g., an IR camera, or the like), a radio frequency sensor, an audio sensor (e.g., a microphone, or the like), or any combination thereof.

The apparatus 100 may include a sensor compartment 120. For example, the sensor compartment 120 may be disposed within the handle 106 or the body 104, or partially within the handle 106 and partially within the body 104. In some embodiments, the one or more sensors may be readily accessible within and/or removable from the sensor compartment 120. For example, the sensor compartment 120 may be a separate compartment coupled to the housing 102 (e.g., positioned within a cut-out in the body 104, the handle 106, or the like). By way of another example, the sensor compartment 120 may be at least partially shielded by a removable plate or cover. For instance, the removable plate or cover may be held in place by an interlocking assembly, fasteners, an adhesive, or the like. By way of another example, the sensor compartment 120 may be removable with the entire handle 106 as a swappable component.

The one or more sensors may be standalone components within the sensor compartment 120. The one or more sensors may be coupled to one or more printed boards. For example, the one or more printed boards may include, but are not limited to, a printed circuit board (PCB), printed wafer board (PWB), or the like.

Although the present disclosure is directed to the one or more sensors of the apparatus 100 being disposed within the sensor compartment 120, it is noted herein that the sensor compartment 120 may not include all sensors installed within the apparatus 100. For example, at least some of the one or more sensors may be located in other areas of the apparatus 100 (e.g., within the body 104, the handle 106, the one or more legs 110, or the like). By way of another example, at least some of the one or more sensors may be located within the user interface device 114. Therefore, the above description should not be interpreted as a limitation on the present disclosure but merely an illustration.

The apparatus 100 may include one or more communication interfaces 122. For example, the one or more communication interfaces 122 may include, but is not limited to, a transceiver. For instance, the transceiver may include a chip that operates via a radio frequency (RF) (e.g., a radio frequency identification (RFID) tag, or the like). In addition, the transceiver may include an emitter that operates via an optical signal (e.g., infrared (IR) emitter, or the like). It is noted herein, however, that the one or more communication interfaces may include one or more transmitters, one or more receivers, or a combination of one or more transmitters and one or more receivers.

The one or more communication interfaces 122 may communicate with one or more external components (e.g., components including one or more passive or active transceivers, transmitters, and/or receivers) to determine the proximity or distance between the one or more communication interfaces 122 and the one or more external components. For example, the time it takes for an emitted RF signal or IR signal to travel between the one or more communication interfaces 122 and the one or more external components, combined with the known propagation speed of the emitted RF signal or IR signal, may provide a distance between the apparatus 100 and the one or more external components.

The apparatus 100 includes one or more signal paths 124. For example, the one or more signal paths 124 may include, but are not limited to, one or more wires, cables, traces, or the like. In embodiments, the one or more signal paths 124 may extend through at least one of the two legs 110 that couple the handle 106 to the body 104. For example, the one or more signal paths 124 may extend from sensors 116, 118 and/or sensor compartment 120 in the handle 106 to the user interface device 114 in the cavity 112 of the body 104.

In some embodiments, the one or more signal paths 124 may include one or more couplers. For example, the one or more couplers may be positioned within the housing 102 proximate to a point of detachment along the one or more legs 110, where the handle 106 may be detached from the body 104.

The apparatus 100 may include one or more communication ports 126. For example, a communication port 126 may include a female (or male) end of a connector set configured to transfer at least one of data and/or power.

In some embodiments, the apparatus 100 includes one or more indicators 128. The one or more indicators 128 may illustrate one or more operational states of the apparatus 100 including, but not limited to, charging, connectivity, data transfer, or the like. The one or more indicators 128 may be positioned on or at least partially inset within one or more surfaces of the housing 102. The one or more indicators 128 may emit a light and/or a sound. For example, where the one or more indicators 128 emit a light, the light-emitting portion of the one or more indicators 128 may be any two-dimensional (2D) shape known in the art. By way of another example, where the one or more indicators 128 emit a light, the light may be any color known in the art.

The one or more signal paths 124 may extend throughout the housing 102. At least some of the one or more sensors 116, 118, the one or more printed boards, the one or more communication interfaces 122, the one or more communication ports 126, or the one or more indicators 128 may include one or more connectors that are couplable to the one or more signal paths 124. For example, the one or more connectors may include, but are not limited to, one or more pins, sockets, or the like. In this regard, at least some of the one or more sensors 116, 118, the one or more printed boards, the one or more communication interfaces 122, the one or more communication ports 126, or the one or more indicators 128 may be in communication via the one or more signal paths 124.

Although the present disclosure is directed to the user interface device 114 being integrated within the housing 102, it is noted herein the user interface device 114 may be an insertable component of the apparatus 100. For example, the housing 102 may include an access point (e.g., door, panel, cover, or the like) to the cavity 112, through which the user interface device 114 may be inserted into the cavity 112. In this example, the cavity 112 may include one or more signal paths 124 (e.g., a connector set configured to transfer at least one of data and/or power, or the like) that extend into the cavity 112 to communicatively couple to an inserted user interface device 114.

Figure 2A:
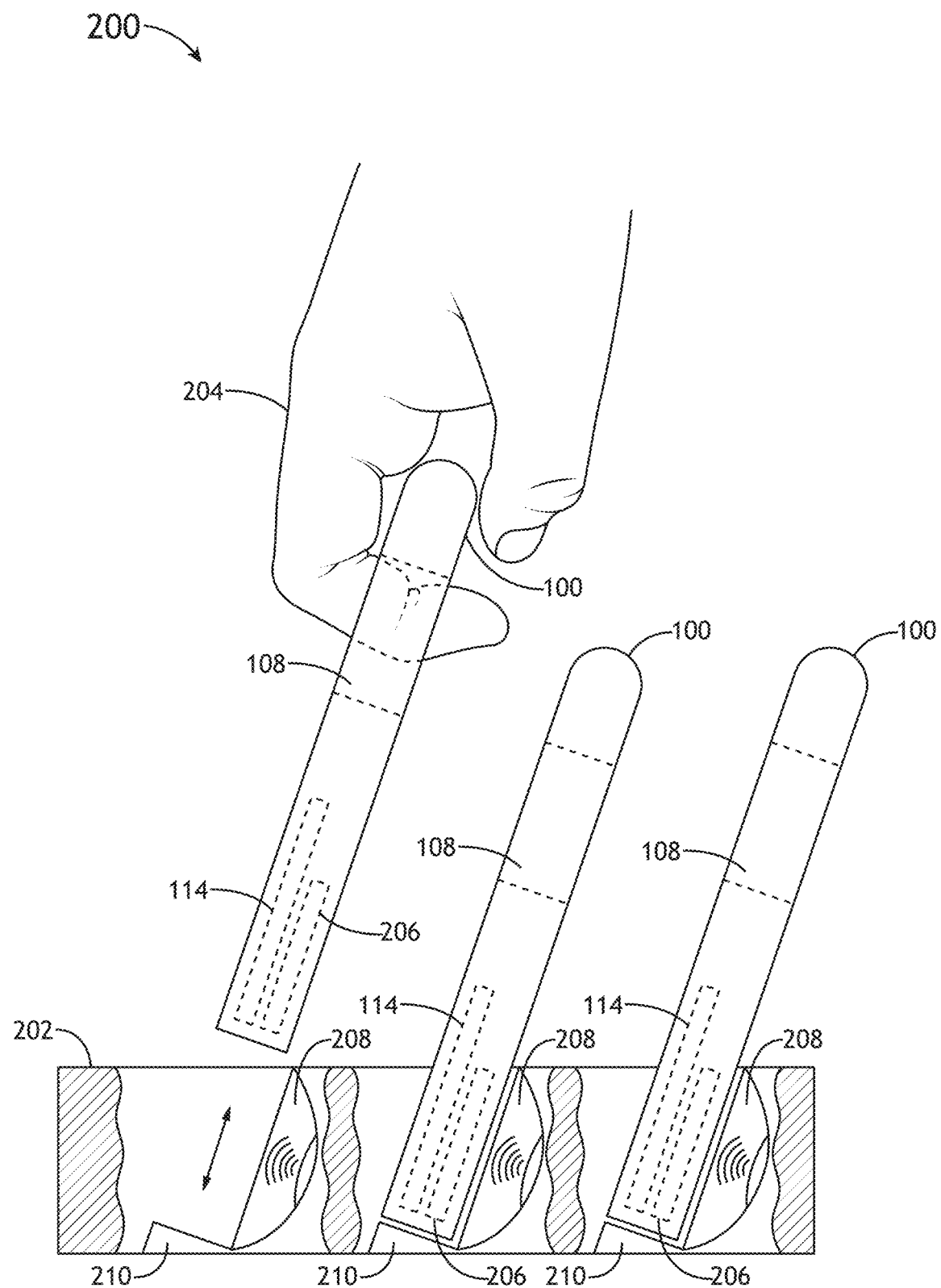
FIG. 2A is a cross-sectional side view of a dock for the apparatus for assessing user frailty, in accordance with an example embodiment of the present disclosure.
Figure 2B:
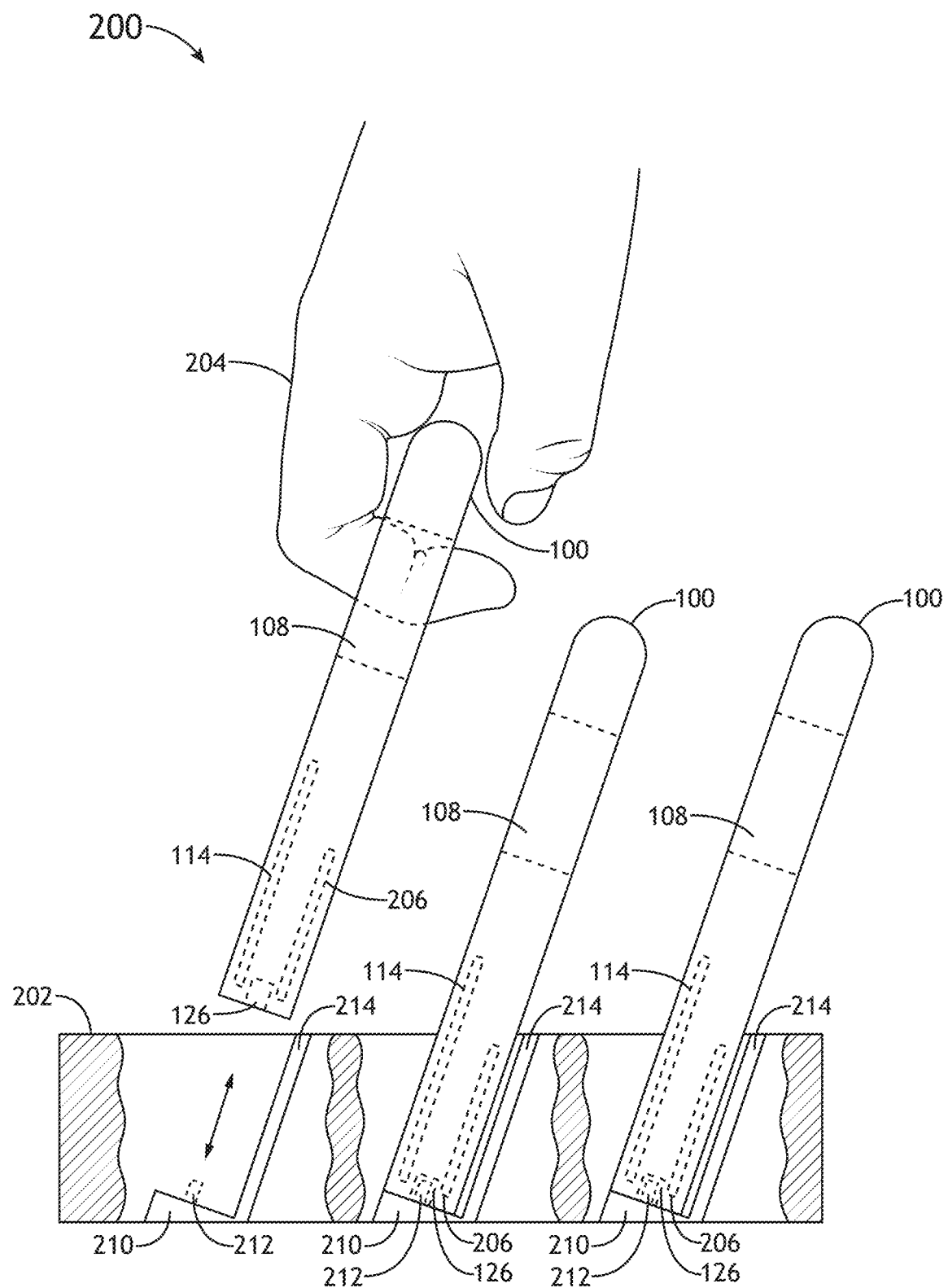
FIG. 2B is a cross-sectional side view of a dock for the apparatus for assessing user frailty, in accordance with an example embodiment of the present disclosure.
Figure 2C:
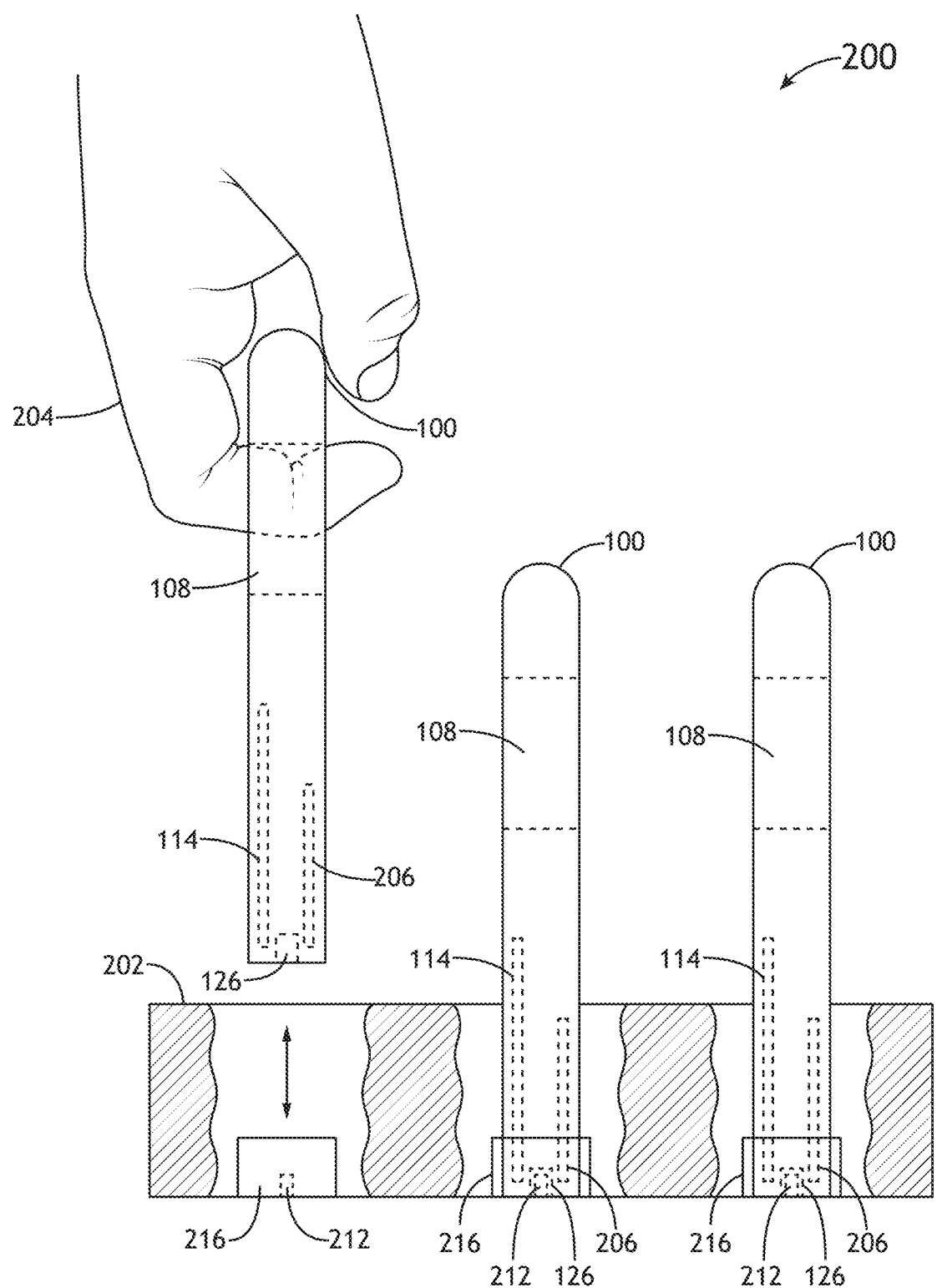
FIG. 2C is a cross-sectional side view of a dock for the apparatus for assessing user frailty, in accordance with an example embodiment of the present disclosure.

FIGS. 2A through 2C illustrate example embodiments of a dock 200 including one or more apparatuses 100 for assessing user frailty. In embodiments, the dock 200 includes a chassis 202 configured to receive and/or interact with one or more apparatuses 100. The one or more apparatuses 100 may be inserted into the chassis 202 such that the cavity 108 is accessible by medical personnel 204 (e.g., a physician's assistant, a physician, or the like). For example, the medical personnel 204 may be able to remove an apparatus 100 from the chassis 202 without interfering with the user interface device 114 of an adjacent apparatus 100.

Figure 3:
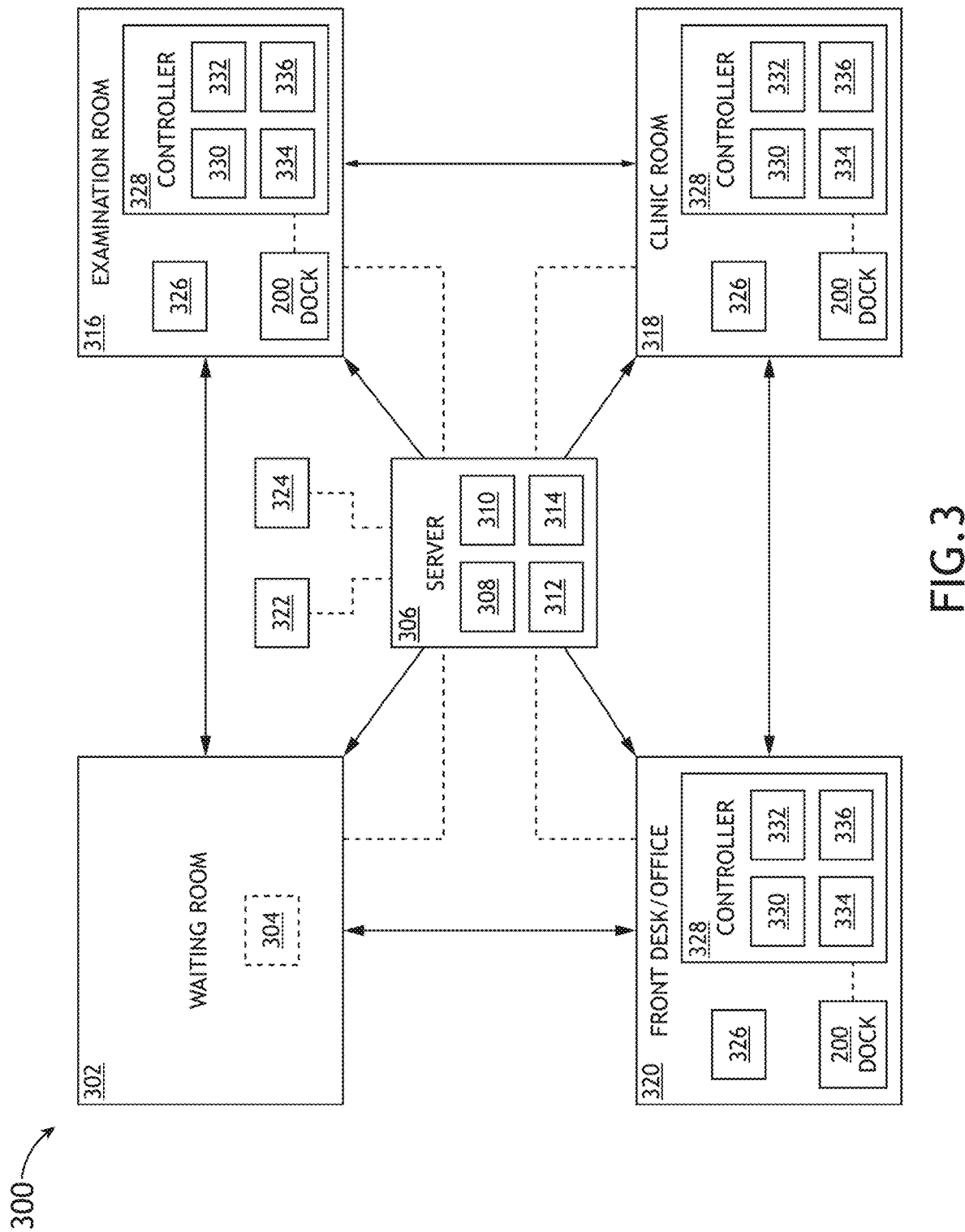
FIG. 3 is a block diagram illustrating an environment in which the apparatus for assessing user frailty may be employed, in accordance with an example embodiment of the present disclosure.
Figure 7:
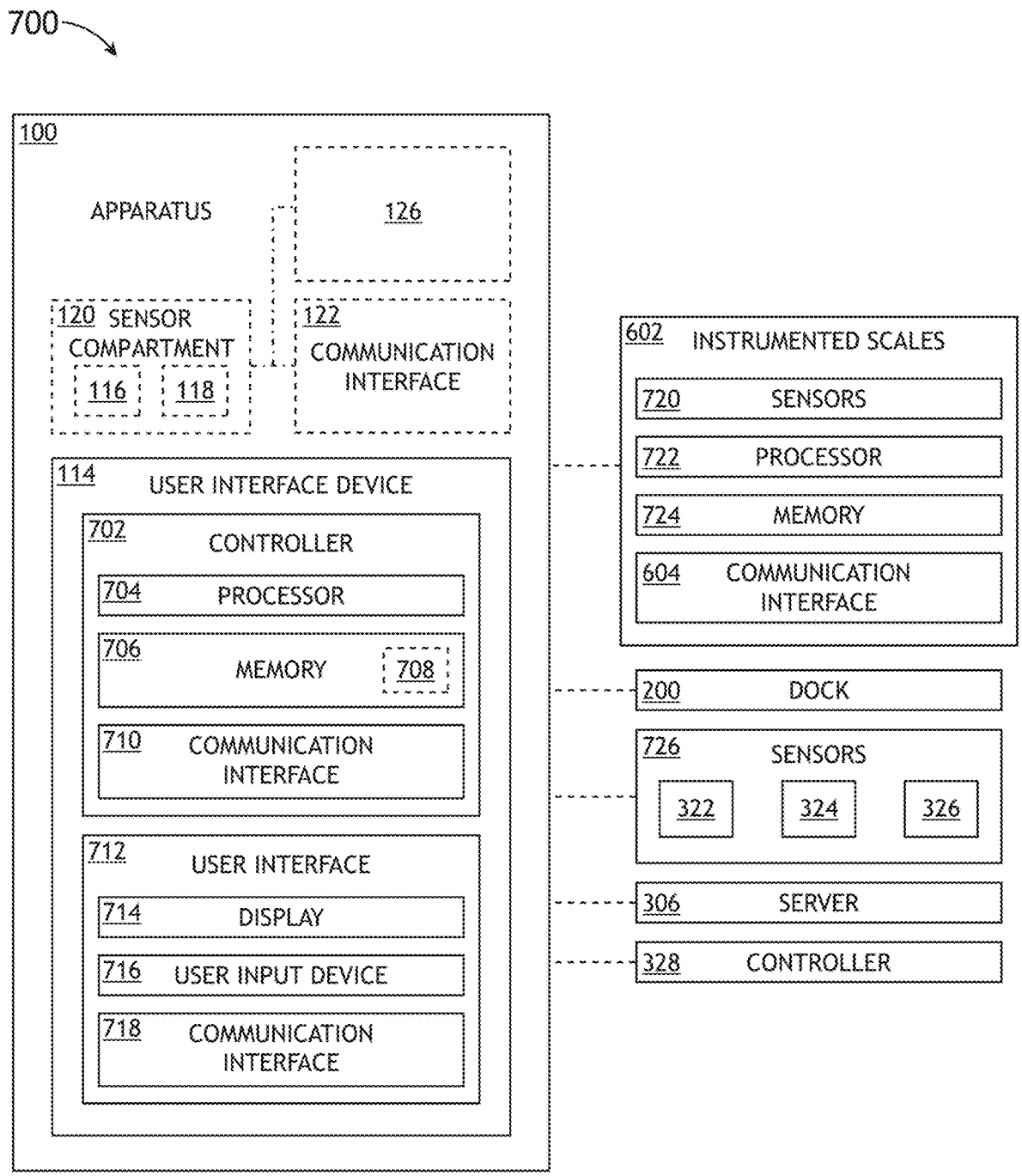
FIG. 7 is a block diagram illustrating a system that includes the apparatus for assessing user frailty, in accordance with an example embodiment of the present disclosure.

The chassis 202 may be configured to transfer power to (e.g., charge) a battery 206 of the apparatus 100. The chassis 202 may be configured to transfer data between the apparatus 100 and one or more components of an external system (e.g., as illustrated in FIGS. 3 and 7). The chassis 202 may include one or more inductive charging surfaces 208 (e.g., as illustrated in FIG. 2A). The chassis 202 may include one or more bases 210. For example, a particular apparatus 100 may be supported by a stand including a particular inductive charging surface 208 and/or a particular base 210. By way of another example, the particular apparatus 100 may be charged via a collective inductive charging surface 208 and supported by a collective base 210.

The chassis 202 may include one or more connectors 212 (e.g., as illustrated in FIGS. 2B and 2C). For example, a connector 212 may include a male end of a connector set (e.g., including the communication port 126) configured to transfer at least one of data and/or power.

In some embodiments, the one or more connectors 212 may extend from the one or more bases 210. The one or more apparatuses 100 may be supported by one or more support structures 214 and the one or more bases 210 (e.g., as illustrated in FIG. 2B). For example, a particular apparatus 100 may be supported by a stand including a particular support structure 214 and/or a particular base 210. By way of another example, the particular apparatus 100 may be supported by a collective support structure 214 and supported by a collective base 210.

In some embodiments, the one or more connectors 212 may extend from a cavity defined within one or more cradles 216 (e.g., as illustrated in FIG. 2C). The one or more apparatuses 100 may be supported by the one or more cradles 216. For example, a particular apparatus 100 may be supported within a particular cradle 216. By way of another example, the particular apparatus 100 may be supported within a collective cradle 216.

Figure 5:
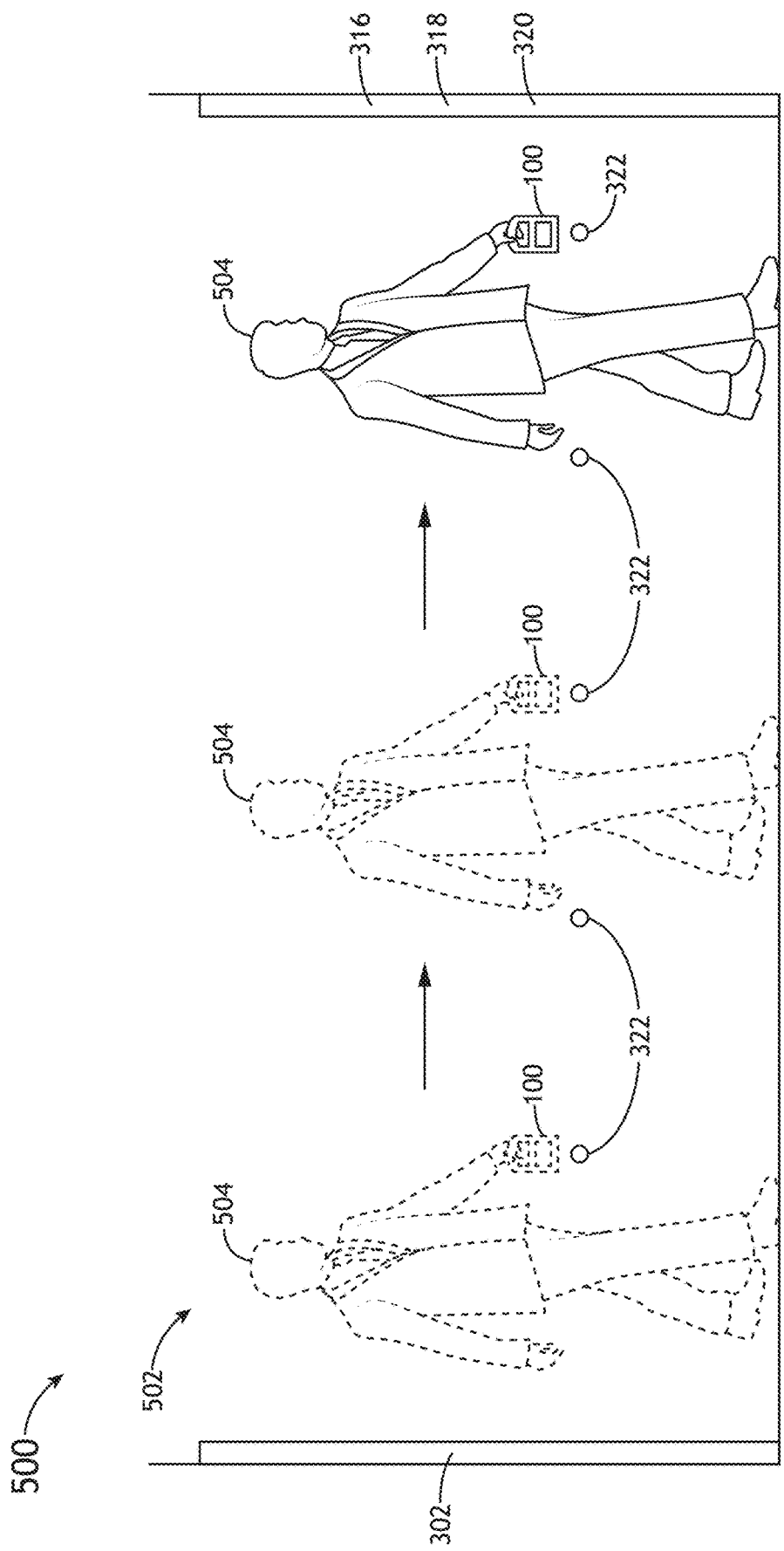
FIG. 5 illustrates an environment in which the apparatus for assessing user frailty may be utilized, in accordance with an example embodiment of the present disclosure.

FIG. 3 illustrates an example embodiment of an environment 300 in which the apparatus 100 for assessing user frailty may be employed. The environment 300 may include, but is not limited to, a hospital, clinic, doctor's office, strength training facility, or other facility known in the art capable of providing medical treatment or conditioning. In embodiments, the environment 300 may include a waiting room 302. A patient (e.g., a patient 504, as illustrated in FIG. 5) may be provided with an apparatus 100 while in the waiting room 302. The patient 504 may use the apparatus 100 to provide initial information in response to prompts from the apparatus 100 and/or prompts on a physical copy.

Figure 4A:
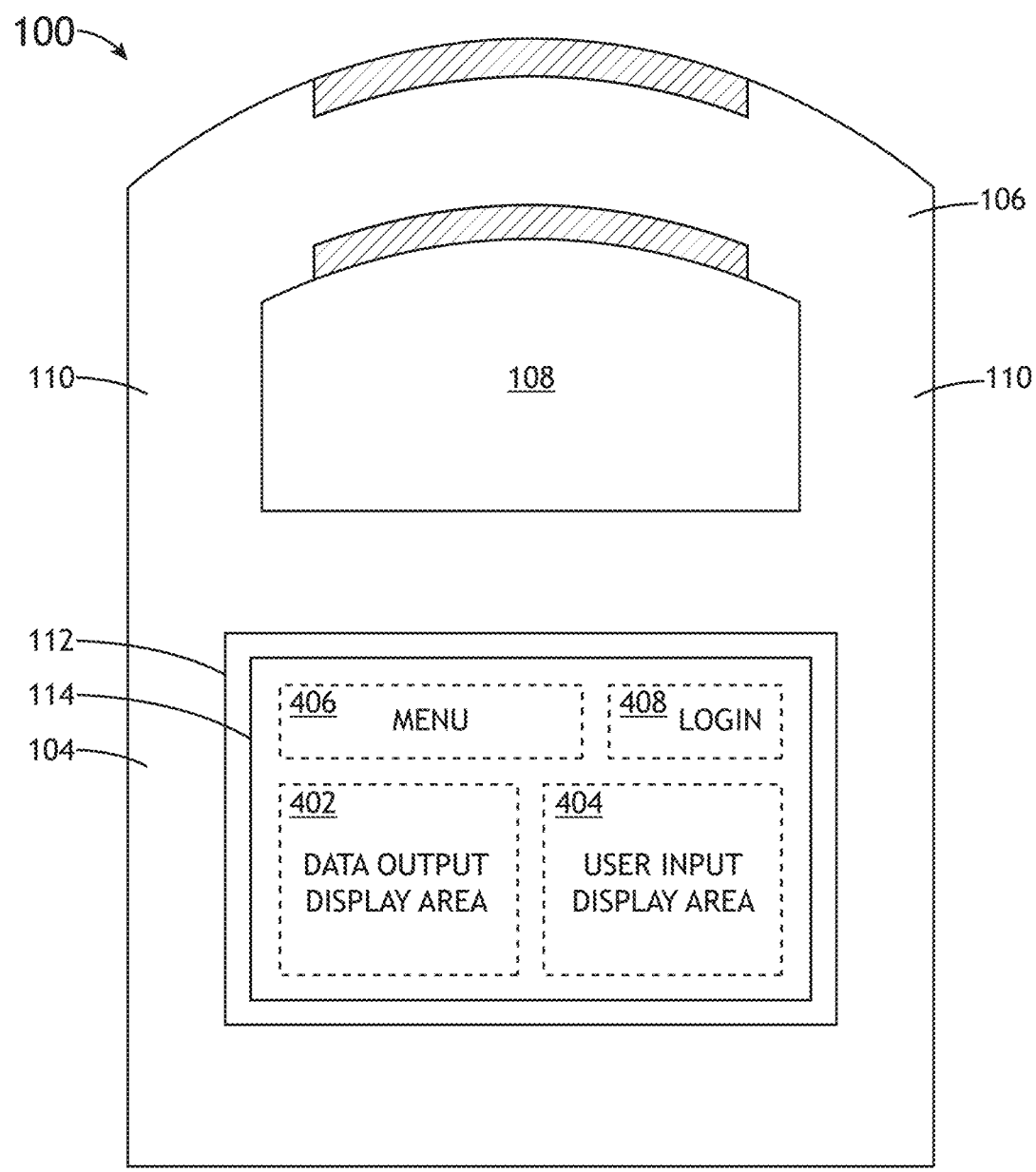
FIG. 4A is a frontal view of an apparatus for assessing user frailty, in accordance with an example embodiment of the present disclosure.

The user interface device 114 may include a graphical user interface (GUI), where the GUI includes one or more GUI windows or GUI display areas. For example, as illustrated in FIG. 4A, the one or more display areas may include, but are not limited to, a data output display area 402, a user input display area 404, a menu display area 406, or a login prompt display area 408. For instance, the data output display area 402 may display content for collecting information (e.g., a patient questionnaire or question bank, a patient file, or the like) to the patient 504. The patient may input data into the user input display area 404 in response to the content displayed within the data output display area 402. It is noted herein the patient may enter information into the user interface device 114 of the apparatus 100 in response to a source of information (e.g., physical copy) separate from the content displayed within the data output display area 402.

Figure 4B:
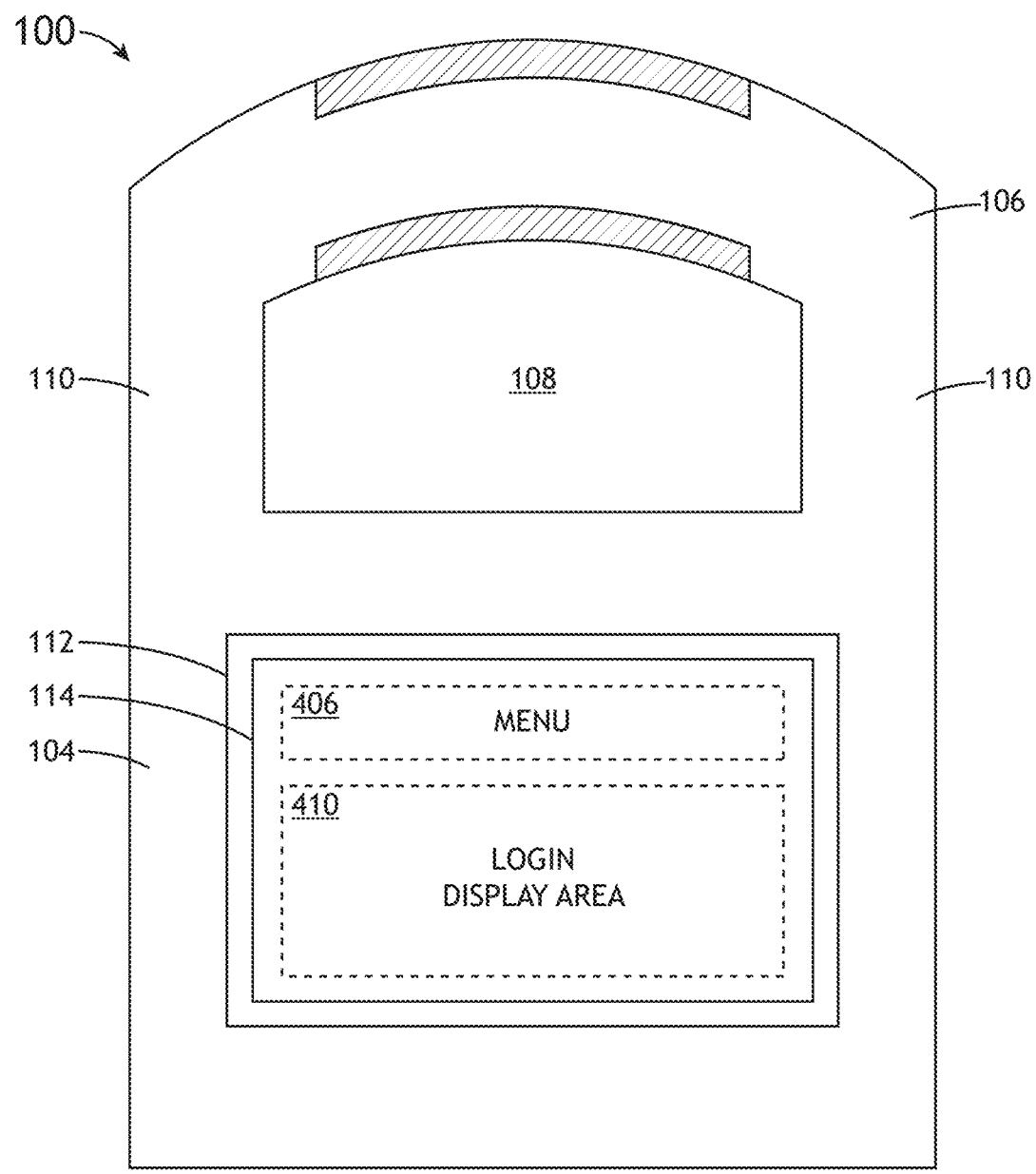
FIG. 4B is a frontal view of an apparatus for assessing user frailty, in accordance with an example embodiment of the present disclosure.

The login prompt display area 408 may return a login display area 410 if interacted with by the patient 504 or the medical personnel 204 (e.g., as illustrated in FIG. 4B). Different users may be directed to different user interface portals based on provided information used to log into the user interface device 114. For example, the inputting of patient log-in credentials may cause the user interface device 114 to provide a patient portal to the patient. By way of another example, the inputting of physician assistant log-in credentials may cause the user interface device 114 to provide a physician assistant portal to a physician's assistant. By way of another example, the inputting of physician log-in credentials may cause the user interface device 114 to provide a physician portal to a physician. Generally, the inputting of log-in credentials may cause the user interface device 114 to provide a relevant and/or portal pre-determined to be accessible by the owner of the credentials.

Referring again to FIG. 3, the information entered into the apparatus 100 (e.g., via the user interface device 114) and/or the information obtained via the one or more sensors 116, 118 may be entered as data 304 into the electronic medical record (EMR) of the patient and/or into a databank (e.g., patient report medical information systems, Medicare registries, or the like) on one or more servers 306. A server 306 may include one or more processors 308 and memory 310. The memory 310 may store one or more executable instructions. The one or more processors 308 may be configured to execute the one or more executable instructions. The server 306 may include one or more communication interfaces 312. The server 306 may include one or more user interfaces 314. For example, the one or more user interfaces 314 may be integrated within a chassis of the server 306 or may be communicatively coupled to the server 306.

The one or more servers 306 may be housed within the environment 300 and managed by in-house personnel. It is noted herein, however, that the one or more servers 306 may be housed within the environment 300 and managed by third-party technicians. In addition, it is noted herein the one or more servers 306 may be housed outside of the environment 300 and managed by third-party technicians. In this regard, the one or more servers 306 may be coupled to the apparatus 100 via one or more direct communication links (e.g., via one or more wired connections), via one or more indirect communication links (e.g., is cloud-based), or via a mixture of direct and indirect communication links.

Following the providing of the initial information in response to prompts, the patient 504 may be moved from the waiting room 302 to an examination room 316, one or more additional clinic rooms 318, and/or a front desk or office 320. For example, the one or more additional clinic rooms 318 may include, but are not limited to, an operating room or the like. The apparatus 100 may travel with the patient, and the patient may be given additional tests on the way to and/or in in the examination room 316, in the one or more additional clinic rooms 318, or at the front desk or office 320.

FIG. 5 illustrates an example embodiment of an environment 500 in which the apparatus 100 for assessing user frailty may be employed. The environment 500 may include one or more hallways 502 connecting the waiting room 302 and the examination room 316, the one or more additional clinic rooms 318, or the front desk or office 320. One or more sensors 322 may be positioned within the hallway 502. For example, the one or more sensors 322 may be positioned at set intervals along the hallway 502. For instance, the one or more sensors 322 may communicate with the one or more communication interfaces 122 of the apparatus 100 via an RF signal, an optical signal (e.g., IR signal), or the like. In this regard, any of the one or more sensors 322 and/or the one or more communication interfaces 122 may include RF emitters, optical signal emitters (e.g., IR emitters), or the like.

As the patient 504 passes by the one or more sensors 322, the one or more sensors 322 may generate data. For example, the data may be related to the ambulatory motion (e.g., walk speed, acceleration, or the like) of the patient. For instance, the walk speed may be calculated from the time it takes the patient to pass each sensor 322 of the one or more sensors 322.

Figure 6A:
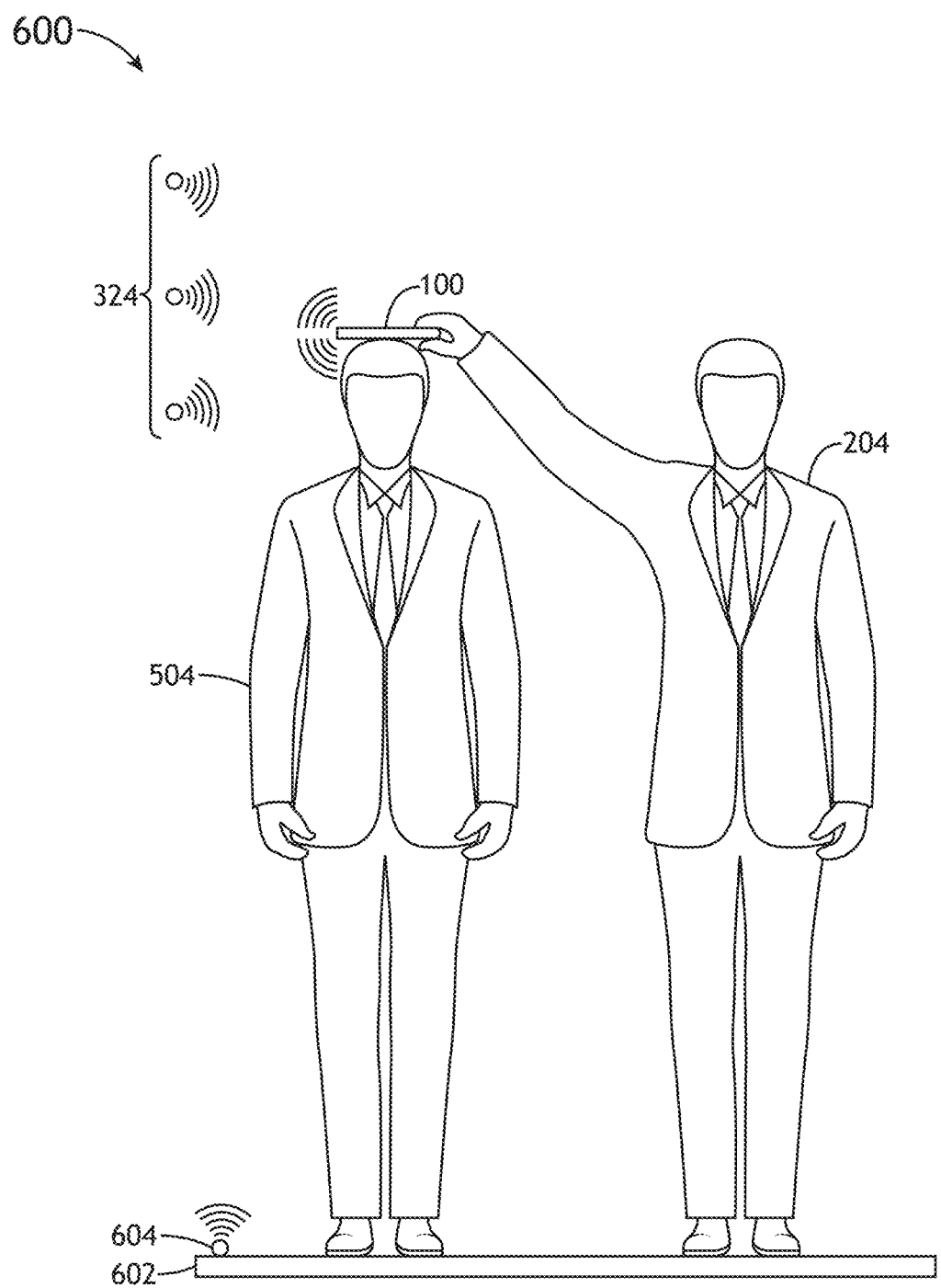
FIG. 6A illustrates an environment in which the apparatus for assessing user frailty may be employed, in accordance with an example embodiment of the present disclosure.
Figure 6B:
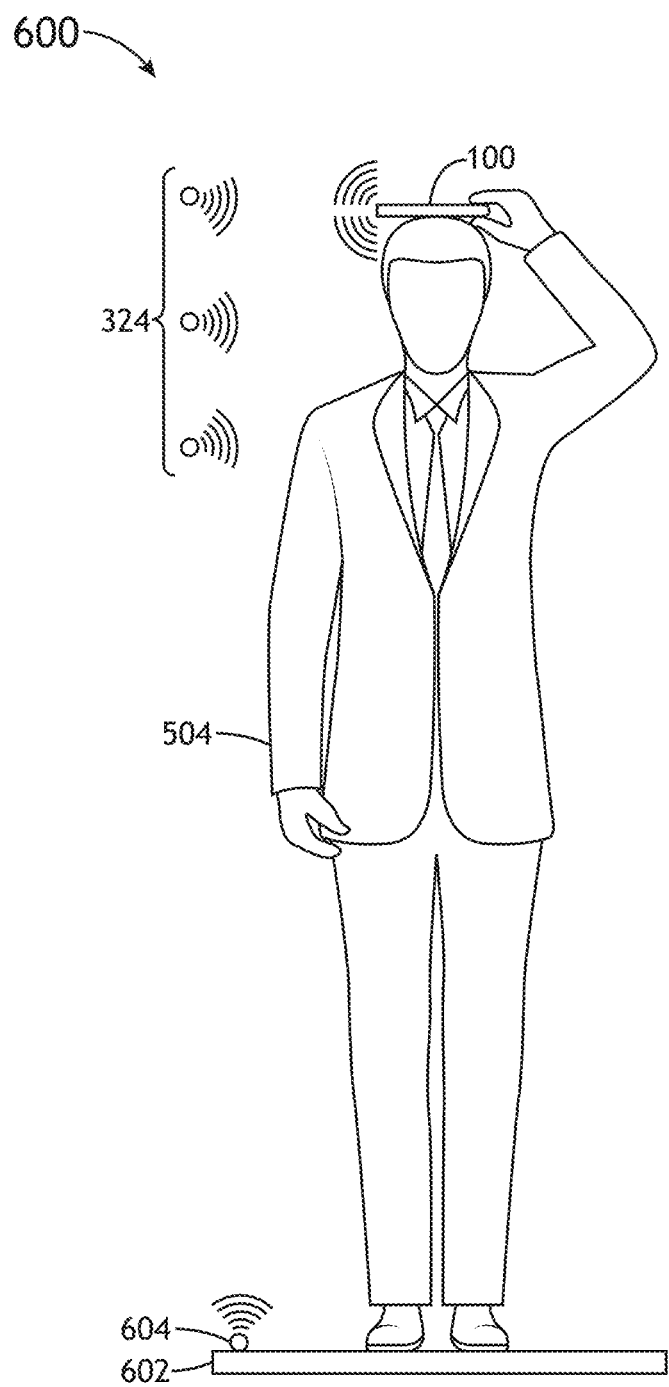
FIG. 6B illustrates an environment in which the apparatus for assessing user frailty may be employed, in accordance with an example embodiment of the present disclosure.

FIGS. 6A and 6B illustrate another example embodiment of an environment 600 in which the apparatus 100 for assessing user frailty may be employed. The environment 600 may include the examination room 316, the one or more additional clinic rooms 318, the front desk or office 320, or the one or more hallways 502. One or more sensors 324 may be positioned within the environment 600. For example, the one or more sensors 324 may be positioned at set intervals within a wall in the environment 600. By way of another example, the one or more sensors 324 may include at least three sensors 324, which may be positioned within the environment 600 to determine a location of the patient 504 via triangulation.

The one or more sensors 324 may generate data for the patient 504 as the patient stands in front of the one or more sensors 324. For example, the data may be related to a height of the patient. For instance, the patient 504 or medical personnel 204 may hold the apparatus 100 on the patient's head. By way of another example, the data may be related to a weight of the patient where the patient stands on an instrumented scale 602.

The instrumented scale 602 may include one or more communication interfaces 604 configured to communicate with the apparatus 100 (e.g., the one or more communication interfaces 122 of the apparatus 100 and/or the one or more sensors 324. For example, the one or more communication interfaces 604 or the one or more sensors 324 may communicate with the one or more communication interfaces 122 of the apparatus 100 via an RF signal, an optical signal (e.g., IR signal), or the like. In this regard, any of the one or more communication interfaces 604, the one or more sensors 324, and/or the one or more communication interfaces 122 may include RF emitters, optical signal emitters (e.g., IR emitters), or the like.

Referring again to FIG. 3, the information obtained via the one or more sensors 322, 324 may be entered as data into the electronic medical record (EMR) of the patient and/or into the databank on the one or more servers 306. The examination room 316, the one or more additional clinic rooms 318, the front desk or office 320 may include one or more additional sensors 326. The one or more additional sensors 326 may generate data for the patient 504. The information obtained via the one or more sensors 326 may be entered as data into the electronic medical record (EMR) of the patient and/or into the databank on the one or more servers 306.

The examination room 316, the one or more additional clinic rooms 318, and/or the front desk or office 320 may include one or more controllers 328. The one or more controllers 328 may be coupled to one or more docks 200. A controller 328 may include one or more processors 330 and memory 332. The memory 332 may store one or more executable instructions. The one or more processors 330 may be configured to execute the one or more executable instructions. The controller 328 may include one or more communication interfaces 334. The controller 328 may include one or more user interfaces 336. For example, the one or more user interfaces 336 may be integrated within a chassis of the controller 328 or may be communicatively coupled to the controller 328.

The controller 328 may be a computer including, but not limited to, a desktop computer, a mainframe computer system, a workstation, an image computer, a parallel processor, a networked computer, or the like. The controller 328 may be a personal electronic device. For example, the personal electronic device may include a handheld computer such as, but not limited to, a smartphone, a tablet, a phablet, or the like. By way of another example, the personal electronic device may include a laptop computer such as, but not limited to, a laptop with a single-fold hinge, a laptop with a double-fold hinge, a laptop with a twist-and-fold hinge, a laptop with a detachable display device and/or a detachable user input device, or the like.

FIG. 7 is a block diagram illustrating an example embodiment of a system 700 that includes the apparatus 100. In embodiments, the user interface device 114 of the apparatus 100 may include a controller 702. The controller 702 may include one or more processors 704 and memory 706. The memory 706 may store one or more executable instructions 708. The one or more processors 704 may be configured to execute the one or more executable instructions 708. The controller 702 may include one or more communication interfaces 710.

The one or more executable instructions 708 may be configured to cause the one or more processors 704 to provide a patient with content for collecting initial information; receive one or more sets of initial information from the patient in response to the provided content for collecting initial information; receive one or more additional sets of information about the patient; entering the one or more sets of information into an electronic medical record (EMR) of the patient; upload the one or more sets of information into a databank stored on one or more servers; determine a frailty level of the patient; and/or provide the frailty level.

A user interface 712 may include, but is not limited to, one or more displays 714, one or more user input devices 716, or one or more communication interfaces 718.

The display 714 may include, but is not limited to, a media display device (e.g., a liquid crystal display (LCD), a light-emitting diode (LED) based display, an organic light-emitting diode (OLED) based display, an electroluminescent display (ELD), an electronic paper (E-ink) display, a plasma display panel (PDP), a display light processing (DLP) display, or the like) for viewing data generated by and/or provided to the user (e.g., the patient 504, medical personnel 204, or the like).

The one or more input devices 716 may include any user input device known in the art. For example, the one or more input devices 716 may include, but are not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device, or the like. For instance, the apparatus 100 may include one or more digital icons that indicate control actions (e.g., play, pause, stop, fast forward, rewind, next, back, on/off, symbol or keystroke input, or the like) associated with respective portions of the user interface 712. In addition, the user interface 712 may include a capacitive touch interface (e.g., a capacitive touchpad, capacitive touchscreen, one or more capacitive touch sensors, a resistive touchscreen, a surface acoustic based touchscreen, an infrared based touchscreen, or the like). Where the user interface 712 is a capacitive touchpad or one or more capacitive touch sensors, the apparatus 100 may include icons formed over (e.g., printed or other applied to) an outer surface of the capacitive touchpad to indicate control actions associated with respective portions of the capacitive touchpad. In addition, the user interface 712 may be a capacitive touchscreen configured to display icons that indicate control actions associated with respective portions of the capacitive touchscreen.

In a general sense, any display 714 capable of integration with the user input device 716 (e.g., touchscreen, bezel mounted interface, keyboard, mouse, trackpad, and the like) is suitable for implementation in the present invention.

The user interface device 114 may include one or more visual input devices (e.g., one or more cameras). The user interface device 114 may include one or more audio input devices (e.g., one or more microphones). The user interface device 114 may include one or more audio output devices (e.g., speaker(s), audio output jack, and/or wireless transmitter (e.g., Bluetooth audio transmitter), or the like).

It is noted herein that any embodiments directed to the user interface 712, the one or more displays 714, and the one or more user input devices 716 may be directed to the user interface 314 and/or the user interface 336. Therefore, the above description should not be interpreted as a limitation on the present disclosure but merely an illustration.

The system 700 may include, but is not limited to, one or more instrumented scales 602. For example, the one or more instrumented scales 602 may include, but are not limited to, one or more sensors 720, one or more processors 722, a memory 724, or the one or more communication interfaces 604. The memory 724 may store one or more executable instructions. The one or more processors 722 may be configured to execute the one or more executable instructions.

The system 700 may include one or more devices external to the apparatus 100. For example, the one or more external devices may include, but are not limited to, one or more docks 200, one or more sensors 726 (e.g., the one or more sensors 322, 324, 326), one or more servers 306, and/or one or more controllers 328.

The one or more processors 308, 330, 704, 722 provides processing functionality and can include any number of processors, micro-controllers, circuitry, field programmable gate array (FPGA) or other processing systems, and resident or external memory for storing data, executable code, and other information accessed or generated (e.g., by at least the server 306, the controller 328, controller 702, or the instrumented scale 602, respectively). The processor 308, 330, 704, 722 can execute one or more software programs embodied in a non-transitory computer readable medium (e.g., memory 310, 332, 706, 724) that implement techniques described herein. The processor 308, 330, 704, 722 is not limited by the materials from which it is formed or the processing mechanisms employed therein and, as such, can be implemented via semiconductor(s) and/or transistors (e.g., using electronic integrated circuit (IC) components), and so forth.

The memory 310, 332, 706, 724 can be an example of tangible, computer-readable storage medium that provides storage functionality to store various data and/or program code (e.g., executable instructions 708, or the like) associated with operation of the processor 308, 330, 704, 722, such as software programs and/or code segments, or other data to instruct the processor 308, 330, 704, 722, to perform the functionality described herein. Thus, the memory 310, 332, 706, 724 can store data, such as a program of instructions for operating the controller 328, 702, including its components (e.g., processor 308, 330, 704, 722, communication interface 312, 334, 710, 604, etc.), and so forth. It should be noted that while a single memory 310, 332, 706, 724 is described, a wide variety of types and combinations of memory (e.g., tangible, non-transitory memory) can be employed. The memory 310, 332, 706, 724 can be integral with the processor 308, 330, 704, 722, can comprise stand-alone memory, or can be a combination of both. Some examples of the memory 310, 332, 706, 724 can include removable and non-removable memory components, such as random-access memory (RAM), read-only memory (ROM), flash memory (e.g., a secure digital (SD) memory card, a mini-SD memory card, and/or a micro-SD memory card), solid-state drive (SSD) memory, magnetic memory, optical memory, universal serial bus (USB) memory devices, hard disk memory, external memory, and so forth.

The communication interface 312, 334, 710, 604 can be operatively configured to communicate with components of the system 700 (e.g., with at least the server 306, the controller 328, controller 702, or the instrumented scale 602). For example, the communication interface 312, 334, 710, 604 can be configured to retrieve data from the processor 308, 330, 704, 722, transmit data for storage in the memory 310, 332, 706, 724, retrieve data from storage in the memory 310, 332, 706, 724, and so forth. The communication interface 312, 334, 710, 604 can also be communicatively coupled with the processor 308, 330, 704, 722 to facilitate data transfer between components of the components of the system 700 (e.g., with at least the server 306, the controller 328, controller 702, or the instrumented scale 602) and the processor 308, 330, 704, 722. It should be noted that while the communication interface 312, 334, 710, 604 is described as components of the system 700 (e.g., components of at least the server 306, the controller 328, controller 702, or the instrumented scale 602), one or more components of the communication interface 312, 334, 710, 604 can be implemented as external components communicatively coupled to the components of the system 700 (e.g., components of at least the server 306, the controller 328, controller 702, or the instrumented scale 602) via one or more wireless connections (e.g., via RF signals, optical signals, Wi-Fi signals, Bluetooth signals, Near-Field Communication (NFC) signals, or the like), via one or more wired connections (e.g., via the one or more communication ports 126), or a combination of wired connections and wireless connections. The communication interface 312, 334, 710, 604 may include or may be coupled to a transmitter, receiver, transceiver, physical connection interface, or any combination thereof.

Figure 8:
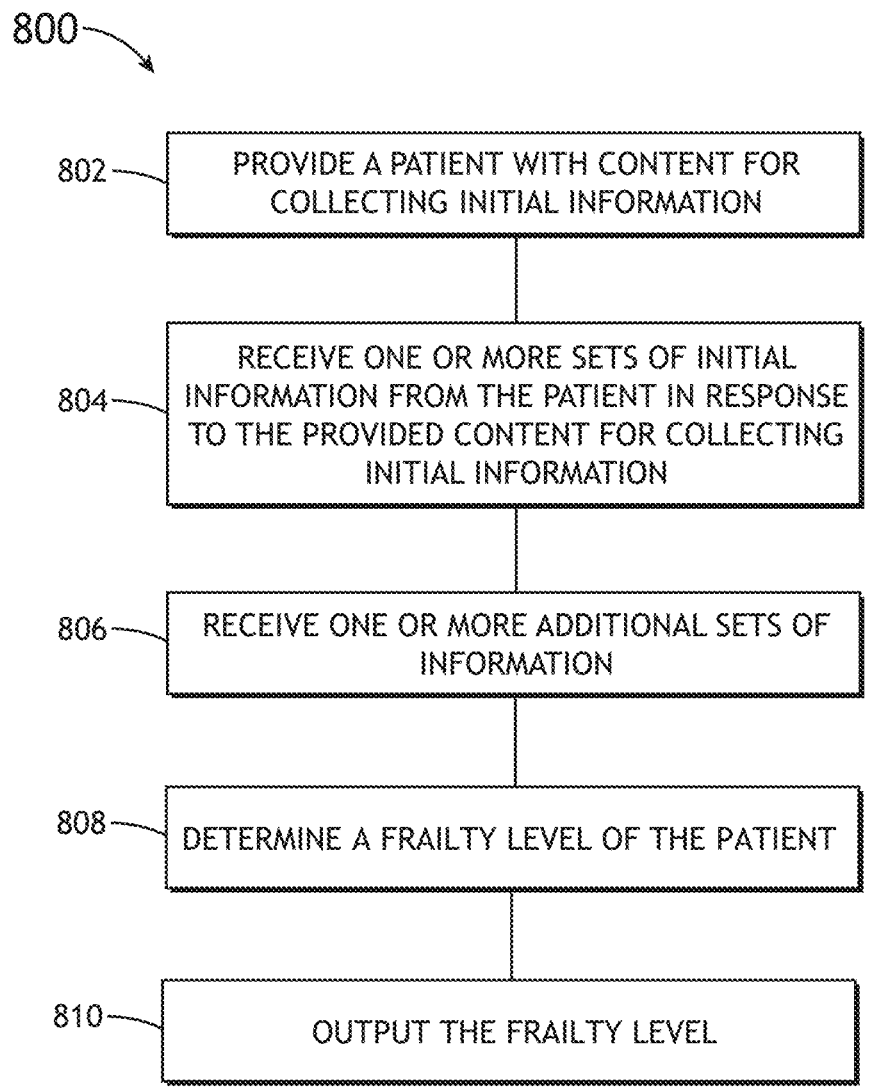
FIG. 8 is a flow diagram illustrating an example implementation of a method for assessing user frailty with an apparatus for assessing user frailty, such as the apparatus illustrated in FIGS. 1 through 7.

FIG. 8 illustrates an example implementation of a method 800 for assessing user frailty with the apparatus 100.

A step 802 may include providing a patient with content for collecting initial information. The content may be displayed on the user interface device 114 of the apparatus 100, and/or may be provided as a physical copy to the patient 504.

A step 804 may include receiving one or more sets of initial information from the patient in response to the provided content for collecting initial information. The patient 504 may input the one or more sets of information into the user interface device 114. The one or more sets of information may include personal information (e.g., name, date of birth, social security number, height, weight, insurer, immunization records, medical screenings, depression screenings, known medical issues, or the like). The one or more sets of information may include data for determining a Risk Analysis Index (RAI) or Deficit Accumulation Index (DAI) of the patient 504. The received one or more sets of information may be entered as the data 304 into the electronic medical record (EMR) of the patient and/or into a databank stored on the one or more servers 306.

A step 806 may include receiving one or more additional sets of information about the patient. The one or more additional sets of information may be obtained via one or more communication interfaces (e.g., communication interfaces 122 of the apparatus 100) or via one or more sensors of the user interface device 114 (e.g., one or more inertial sensors). The one or more additional sets of information may be obtained via one or more sensors within a surrounding environment (e.g., sensors 720 within the instrumented scale 602, sensors 726 including sensors 322, 324, 326, or the like). The one or more additional sets of information may be obtained via an analysis of and/or a consultation with the patient 504 by medical personnel 204. The one or more additional sets of information may include, but are not limited to, phenotypic measurements. For example, the phenotypic measurement may include, but are not limited to, measurement of vitals, (e.g., heart rate, blood pressure, blood oxygen levels, body temperature, or the like), grip strength, ambulatory motion (e.g., timed-up-and-go, chair or stand rises, walk speed, acceleration, or the like), short physical performance battery data, or the like. For instance, the apparatus 100 may include one or more components necessary (e.g., metal band, optical sensors, or the like) to measure blood oxygen levels.

A step 808 may include determining a frailty level of the patient. The frailty level may be determined from the one or more sets of initial information and the one or more additional sets of information about the patient 504. The frailty level may be determined by the controller 702 of the user interface device 114. For example, the controller 702 may be configured to compare the one or more sets of initial information and the one or more additional sets of information to known data for a particular age, height, weight, sex, or the like. In this regard, the user interface device 114 may be able to make more specific comparisons to known data, as opposed to merely comparing to normative values of collected data stored within a dynamometer.

A step 810 may include outputting the frailty level. The frailty level may be provided to the patient 504 as a standalone metric or as one metric of a set of metrics (e.g., during the analysis of and/or the consultation with the patient 504 by medical personnel 204, or the like). The frailty level may be provided to medical personnel 204 as a standalone metric or as one metric of a set of metrics (e.g., via step 906 and/or step 908, as described in detail further herein).

Figure 9:
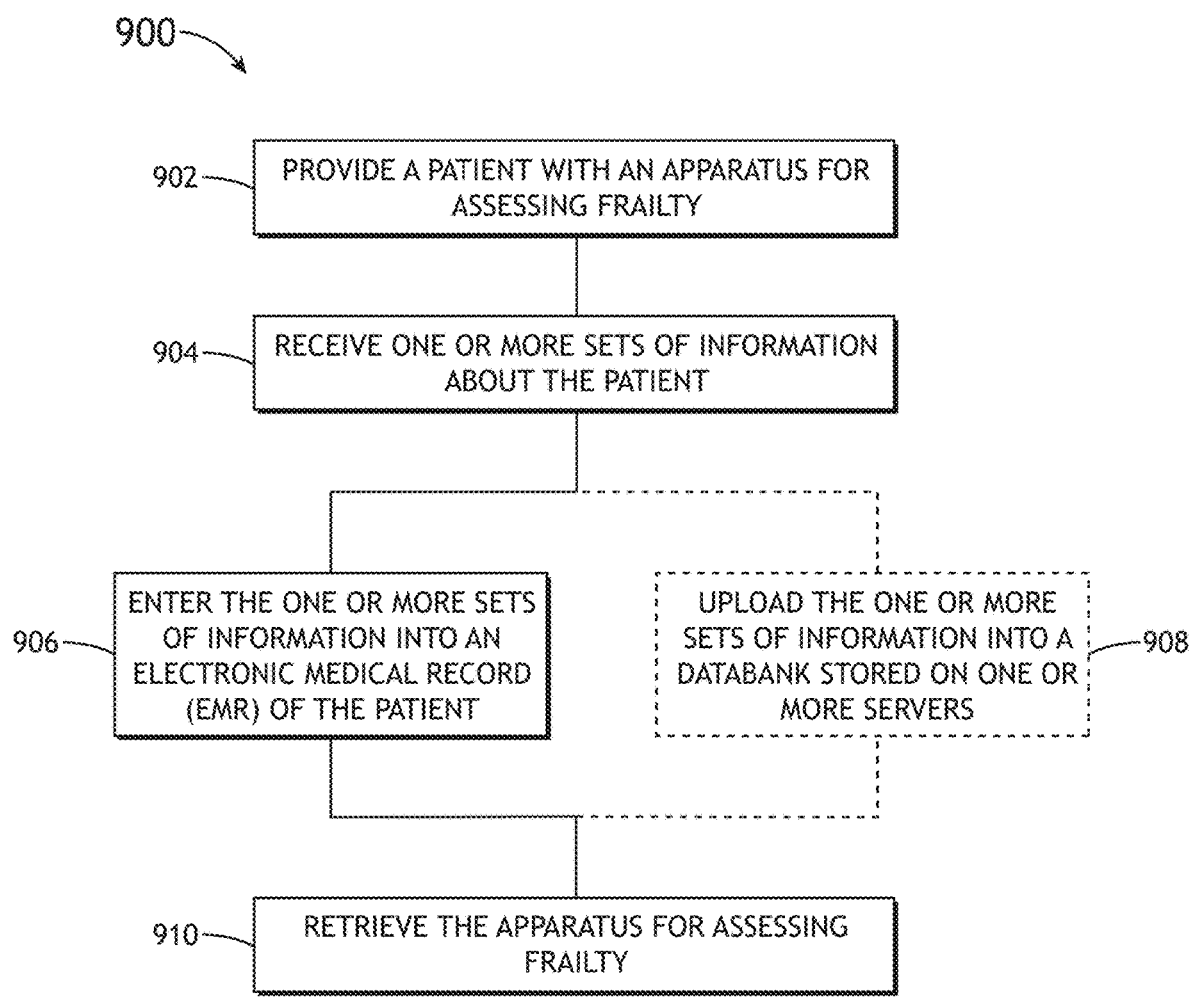
FIG. 9 is a flow diagram illustrating an example implementation of a method for collecting and transferring information with an apparatus for assessing user frailty, such as the apparatus illustrated in FIGS. 1 through 7.

FIG. 9 illustrates an example implementation of a method 900 for collecting and transferring information with the apparatus 100.

A step 902 may include providing a patient with an apparatus for assessing user frailty. The apparatus 100 may be retrieved from the dock 200 by medical personnel 204 and provided to the patient 504.

A step 904 may include retrieving one or more sets of information about the patient. The one or more sets of information may include one or more sets of initial information and/or one or more sets of additional information retrieved via one or more steps of the method 800.

A step 906 may include entering the one or more sets of information into an electronic medical record (EMR) of the patient. An optional step 908 may include uploading the one or more sets of information into a databank stored on one or more servers. The one or more sets of information may be entered via one or more wireless connections (e.g., via Wi-Fi signals, Bluetooth signals, Near-Field Communication (NFC) signals, or the like), via one or more wired connections (e.g., via the one or more communication ports 126 of the apparatus 100, through the dock 200 via the one or more communication ports 126, or the like), or via a combination of wired connections and wireless connections. The one or more sets of information may be manually entered into the EMR and/or uploaded to the one or more servers 306 by an individual with access (e.g., medical personnel 204, authorized third-party technician, or the like). It is noted herein, however, the one or more sets of information may be entered into the EMR and/or uploaded to the one or more servers 306 via one or more automated processes.

It is noted herein the one or more sets of information may be entered into the electronic medical record (EMR) of the patient and/or uploaded into the databank stored on one or more servers at any stage in either method 900 or method 800. Therefore, the above description should not be interpreted as a limitation on the scope of the present disclosure, but merely an illustration.

A step 910 may include retrieving the apparatus for assessing user frailty. The apparatus 100 may be returned to the dock 200 by medical personnel 204 after completion of an analysis of and/or a consultation with the patient 504 by medical personnel 204.

It is noted herein the methods 800 and 900 are not limited to the steps provided. For example, the methods 800 and 900 may instead include more or fewer steps. By way of another example, the methods 800 and 900 may perform the steps in an order other than provided. Therefore, the above description should not be interpreted as a limitation on the scope of the present disclosure, but merely an illustration.

In embodiments, the apparatus 100 may be sent home with a patient 504 for continued assessment of the patient 504. The patient 504 may be required to periodically check in with medical personnel 204 to provide data collected by the apparatus 100. It is noted herein, however, that the apparatus 100 may provide the collected data to medical personnel 204 via one or more automated processes. For example, the apparatus 100 may be wireless (e.g., via Wi-Fi signals, Bluetooth signals, Near-Field Communication (NFC) signals, or the like) capabilities and/or wired connections.

It is to be understood that implementations of the methods disclosed herein may include one or more of the steps described herein. Further, such steps may be carried out in any desired order and, in some implementations, two or more of the steps may be carried out simultaneously with one another. Two or more of the steps disclosed herein may be combined in a single step, and in some implementations, one or more of the steps may be carried out as two or more sub-steps. Further, other steps or sub-steps may be carried in addition to, or as substitutes to one or more of the steps disclosed herein.

Although the technology has been described with reference to the embodiments illustrated in the attached drawing figures, equivalents may be employed and substitutions made herein without departing from the scope of the technology as recited in the claims. Components illustrated and described herein are merely examples of a device and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. An apparatus for assessing user frailty, comprising:
  a housing including:
    a body;
    a cavity defined within the body;
    a handle coupled to the body by two legs; and
    a sensor compartment disposed within the handle;
  a force sensor at least partially disposed within the sensor compartment;
  an inertial sensor at least partially disposed within the housing;
  a user interface device at least partially disposed within the cavity, the user interface device being coupled to the force sensor and the inertial sensor via one or more signal paths between the handle and the body, the user interface device including:
    a controller; and
    a touchscreen coupled to the controller; and
  a communication interface at least partially disposed within the housing, wherein the user interface device is coupled to the communication interface via the one or more signal paths, and wherein the controller is configured to:
    receive height data, via the communication interface, based on triangulation with RF signals from at least three wall-mounted sensors to determine a location of the apparatus when the apparatus is held on a head of a user while the user is standing; and
    determine at least one health metric for the user based on the received height data.

2. The apparatus of claim 1, wherein the one or more signal paths extend through at least one of the two legs that couple the handle to the body.

3. The apparatus of claim 1, wherein the controller is configured to:
  receive grip strength data generated by the user via the force sensor; and
  determine at least one grip strength metric for the user based on the received grip strength data.

4. The apparatus of claim 1, wherein the controller is configured to:
  receive ambulatory mobility data generated by the user via the inertial sensor; and
  determine the at least one health metric for the user based on the received ambulatory mobility data.

5. The apparatus of claim 1, wherein the controller is configured to:
  receive timed-up-and-go data generated by the user via the inertial sensor; and
  determine the at least one health metric for the user based on the received timed-up-and-go data.

6. The apparatus of claim 1, wherein the controller is configured to:
receive weight data for the user from an instrumented scale via the communication interface; and
determine the at least one health metric for the user based on the received weight data.

7. The apparatus of claim 1, further comprising:
at least one additional sensor including at least one of a blood oxygen sensor, a blood pressure sensor, a heart-rate sensor, or a temperature sensor.

8. The apparatus of claim 1, wherein the housing further includes at least one external connector, wherein the at least one external connector is configured to interface with at least one docking station connector, wherein the apparatus is one of a plurality of apparatuses, and wherein the apparatus is configured to be docked alongside the plurality of apparatuses within a docking station.

9. A system, comprising:
a server;
at least one apparatus for assessing user frailty coupled to the server via at least one communication link, the at least one apparatus comprising:
a housing including:
a body;
a cavity defined within the body;
a handle coupled to the body by two legs; and
a sensor compartment disposed within the handle;
a force sensor at least partially disposed within the sensor compartment;
an inertial sensor at least partially disposed within the housing;
a user interface device at least partially disposed within the cavity, the user interface device being coupled to the force sensor and the inertial sensor via one or more signal paths between the handle and the body, the user interface device including:
a controller; and
a touchscreen coupled to the controller; and
a communication interface at least partially disposed within the housing, wherein the user interface device is coupled to the communication interface via the one or more signal paths, and wherein the controller is configured to:
receive height data, via the communication interface, based on triangulation with RF signals from at least three wall-mounted sensors to determine a location of the apparatus when the at least one apparatus is held on a head of a user while the user is standing; and
determine at least one health metric for the user based on the received height data.

10. The system of claim 9, wherein the one or more signal paths extend through at least one of the two legs that couple the handle to the body.

11. The system of claim 9, wherein the controller is configured to:
receive grip strength data generated by the user via the force sensor; and
determine at least one grip strength metric for the user based on the received grip strength data.

12. The system of claim 9, wherein the controller is configured to:
receive ambulatory mobility data generated by the user via the inertial sensor; and
determine the at least one health metric for the user based on the received ambulatory mobility data.

13. The system of claim 9, wherein the controller is configured to:
receive timed-up-and-go data generated by the user via the inertial sensor; and
determine the at least one health metric for the user based on the received timed-up-and-go data.

14. The system of claim 9, wherein the controller is configured to:
receive weight data for the user from an instrumented scale via the communication interface; and
determine the at least one health metric for the user based on the received weight data.

15. The system of claim 9, wherein the housing further includes:
at least one additional sensor including at least one of a blood oxygen sensor, a blood pressure sensor, a heart-rate sensor, or a temperature sensor.

16. The system of claim 9, further comprising:
a docking station with a plurality of docking station connectors, wherein the housing further includes at least one external connector, wherein the at least one external connector is configured to interface with at least one docking station connector of the plurality of docking station connectors, wherein the at least one apparatus is one of a plurality of apparatuses, and wherein the at least one apparatus is configured to be docked alongside the plurality of apparatuses within the docking station.

17. An apparatus for assessing user frailty, comprising:
a body;
a handle coupled to the body by two legs;
a sensor compartment disposed within the handle;
a force sensor at least partially disposed within the sensor compartment;
a cavity defined within the body, the cavity configured to receive a personal electronic device that includes an inertial sensor and a controller;
one or more signal paths configured to couple the personal electronic device to the force sensor; and
a communication interface at least partially disposed within the body, wherein the personal electronic device is coupled to the communication interface via the one or more signal paths, and wherein the controller is configured to:
receive height data, via the communication interface device, based on triangulation with RF signals from at least three wall-mounted sensors to determine a location of the apparatus when the apparatus is held on a head of a user while the user is standing; and
determine at least one health metric for the user based on the received height data.

18. The apparatus of claim 17, wherein the personal electronic device comprises at least one of a smartphone or a tablet.

19. The apparatus of claim 17, wherein the one or more signal paths extend through at least one of the two legs that couple the handle to the body.

20. The apparatus of claim 17, further comprising:
at least one additional sensor including at least one of a blood oxygen sensor, a blood pressure sensor, a heart-rate sensor, or a temperature sensor.

\* \* \* \* \*